US008512351B2

(12) United States Patent
Teague

(10) Patent No.: US 8,512,351 B2
(45) Date of Patent: *Aug. 20, 2013

(54) RELEASABLE MEDICAL BASKET AND RELATED METHODS OF USE

(75) Inventor: James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/347,254

(22) Filed: Jan. 10, 2012

(65) Prior Publication Data

US 2012/0179180 A1    Jul. 12, 2012

Related U.S. Application Data

(63) Continuation of application No. 10/981,642, filed on Nov. 5, 2004, now Pat. No. 8,118,816.

(51) Int. Cl.
*A61B 17/22* (2006.01)

(52) U.S. Cl.
USPC ........................................................ 606/113

(58) Field of Classification Search
USPC ................. 606/110, 113, 114, 127, 128, 200; 623/1.12, 1.15, 1.16, 1.2
See application file for complete search history.

(56) References Cited

U.S. PATENT DOCUMENTS

| 5,324,304 | A | 6/1994 | Rasmussen |
| 5,782,839 | A | 7/1998 | Hart et al. |
| 5,827,324 | A | 10/1998 | Cassell et al. |
| 5,860,987 | A | 1/1999 | Ratcliff et al. |
| 6,059,796 | A | 5/2000 | Bilitz et al. |
| 6,383,193 | B1 | 5/2002 | Cathcart et al. |
| 6,685,722 | B1 | 2/2004 | Rosenbluth et al. |
| 6,800,080 | B1 | 10/2004 | Bates |
| 2004/0138677 | A1 | 7/2004 | Little et al. |
| 2004/0193209 | A1 | 9/2004 | Pavcnik et al. |
| 2007/0005095 | A1 | 1/2007 | Osborne et al. |

OTHER PUBLICATIONS

International Search Report for PCT/US2005/039873 dated Apr. 11, 2006.
Written Opinion of the International Searching Authority for CT/US2005/039873 dated Apr. 11, 2008.

*Primary Examiner* — Ryan Severson
(74) *Attorney, Agent, or Firm* — Bookoff McAndrews, PLLC

(57) ABSTRACT

A device and related methods of use are provided for the capture and removal of various unwanted objects present within the body's anatomical lumens. In an embodiment of the present disclosure, the device includes a sheath, an elongate member, and a retrieval assembly connected to the elongate member and retractable within and extendable from a lumen of the sheath. The device includes one or more legs releasably connected to a portion of the retrieval assembly in response to movement of the elongate member relative to the sheath.

19 Claims, 5 Drawing Sheets

RELEASABLE MEDICAL BASKET AND RELATED METHODS OF USE

This application is a continuation of application Ser. No. 10/981,642, filed Nov. 5, 2004, now U.S. Pat. No. 8,118,816 which is incorporated herein by reference.

FIELD OF THE INVENTION

Embodiments of this invention relate generally to medical devices and procedures. In particular, embodiments of the instant invention relate to medical devices and procedures for assisting in the capture and release of tissue or foreign matter from a body portion.

BACKGROUND OF THE INVENTION

Organic material (e.g., blood clots, tissue, and biological concretions such as urinary, biliary, and pancreatic stones) or inorganic material (e.g., components of medical devices or other foreign matter) may sometimes obstruct or otherwise be present within the body's anatomical lumens, such as the biliary tree. For example, biological concretions can develop in certain parts of the body, such as kidneys, pancreas, and gallbladder. Minimally invasive medical procedures generally involve causing limited trauma to the tissues of the patient, and can be used to dispose of certain problematic biological concretions or similarly unwanted obstructions.

In addition, lithotripsy and ureteroscopy, for example, may also be used to treat biological concretions (e.g., kidney stones) in the body of patients. Lithotripsy is a medical procedure that uses energy in various forms, such as acoustic shock waves, pneumatic pulsation, electro-hydraulic shock waves, or laser beams, to pulverize biological concretions such as urinary calculi (e.g., kidney stones). The force of the energy, when applied either extracorporeally or intracorporeally, usually in focused and continuous or successive bursts, divides the concretion into smaller fragments that may be extracted from the body, or allowed to pass from the body, for example, through urination.

In certain instances, intracorporeal fragmentation of bodily concretions can become problematic if the stones or stone fragments, instead of progressing out of the patient's body, begin to migrate further into the body or towards an organ. In these circumstances, further medical intervention to prevent aggravation of the patient's condition may become necessary. Therefore, it may be desirable to be able to extract such fragments from the body using a single instrument, preventing the need for successive instrumentation which can cause greater trauma to the patient's tissues.

Many medical retrieval devices can be used to entrap an object, such as a stone fragment, and drag it through an ampulla (i.e., a small dilatation in the patient's anatomical lumen) to remove it. Such medical retrieval devices include, for example, retrieval baskets and may be used through an endoscope or laparoscope. However, occasionally an object may be too large to be extracted through an ampulla, or an obstacle is encountered upon forward movement of the stone fragment within the anatomical lumen. It may be necessary to provide further treatment, for example, lithotripsy or surgery.

With many known retrieval assemblies, it is difficult to release entrapped material, such as a stone, from the retrieval assembly once the material is entrapped. For example, in some patients, a cicatrix or some other constriction that reduces the diameter of a body lumen may form within the lumen. The narrowed lumen may not interfere or prevent normal insertion of a retrieval device. However, after the retrieval device is inserted into the tract, the retrieval assembly expands, and an object is captured within the device. At this point, the diameter of the retrieval assembly containing the entrapped object may exceed the inner diameter of the narrowed lumen. Under these circumstances, it may be desirable to release the entrapped object from within the retrieval assembly so that the retrieval assembly may be safely removed from the lumen. Other circumstances may be encountered during a medical retrieval procedure that may also require releasing an entrapped object from the retrieval device.

The present disclosure provides medical retrieval devices and methods of using the same that address some or all of the aforementioned shortcomings of the existing devices.

SUMMARY OF THE INVENTION

Embodiments of the invention provide a medical device and procedure that assists practitioners in the removal of tissue or foreign matter from a desired body portion by entrapment and releases the tissue or foreign matter from entrapment when desired.

In accordance with an aspect of the present disclosure, a medical device may include a sheath having a proximal end, a distal end, and a lumen extending longitudinally between the proximal and distal ends; an elongate member extending within the lumen of the sheath and moveable relative to the sheath; and a retrieval assembly connected to a distal region of the elongate member, retractable within and extendable from the lumen of the sheath, and having a plurality of legs, wherein an end of a leg is configured to be selectively disconnectable from a portion of the retrieval assembly in response to movement of the elongate member relative to the sheath.

In another aspect of the present disclosure, a medical device may include: a sheath having a proximal end, a distal end, and a lumen extending longitudinally between the proximal and distal ends; an elongate member extending within the lumen of the sheath and moveable relative to the sheath; and a retrieval assembly having a proximal end, a distal end, and a plurality of legs, each leg having connections at the proximal and distal ends of the retrieval assembly, the retrieval assembly being connected to a distal region of the elongate member and retractable within and extendable from the lumen of the sheath, wherein a leg is configured to be selectively disconnected from a portion of the retrieval assembly.

In yet another aspect of the present disclosure, a medical device may include: a sheath having a proximal end, a distal end, and a lumen extending longitudinally between the proximal and distal ends; an elongate member extending within the lumen of the sheath and moveable relative to the sheath; and a retrieval assembly connected to a distal region of the elongate member, retractable within and extendable from the lumen of the sheath, and including a plurality of legs, wherein a leg has a first state in which a proximal end of the leg is releasably connected to a portion of the retrieval assembly and second state in which the proximal end of the leg is disconnected from the portion of the retrieval assembly.

Various embodiments of the invention may include one or more of the following aspects: the retrieval assembly may be configured to be substantially collapsed when retracted into the sheath and expanded when extended from the sheath; the leg may be configured to be disconnected in response to movement of the elongate member relative to the sheath; each of two or more legs may have a first state in which the proximal end of the leg is releasably connected to the portion of the retrieval assembly and a second state in which the proximal end of the leg is disconnected from the portion of the retrieval assembly; an end of each of two or more legs may be configured to be selectively disconnectable from the portion of the retrieval assembly in response to movement of the elongate member relative to the sheath; the elongate member and the retrieval assembly may comprise a one-piece construction; the elongate member may be connected to a proximal end of the retrieval assembly; the retrieval assembly may comprise a plurality of spaces between the legs further comprising a means for selectively disconnecting the end of the leg from the retrieval assembly; the selectively disconnecting means may include a portion of the leg configured to be received in an aperture in the portion of the retrieval assembly; the portion of the leg may be confined within the aperture by the sheath while the end of the leg is selectively connected to the portion of the retrieval assembly; the portion of the leg may be released from the aperture in response to movement of the elongate member relative to the sheath; the sheath may be moved proximally to release the portion of the leg from the aperture; the elongate member may be moved distally to release the portion of the leg from the aperture; the end of the leg may be configured to be selectively connected to the portion of the retrieval assembly when the retrieval assembly is retracted within or extended from the lumen of the sheath; the end of the leg may be configured to be selectively connected to the portion of the retrieval assembly when the retrieval assembly is collapsed or expanded; the end of the leg configured to be selectively disconnectable may be free from the portion of the retrieval assembly when in a disconnected state.

A further aspect of the present disclosure includes a method of entrapping an object within a body. The method includes inserting a medical device into a body lumen, the medical device having a sheath having a proximal end, a distal end, and a lumen extending longitudinally between the proximal and distal ends, an elongate member extending within the lumen of the sheath, and a retrieval assembly connected to a distal region of the elongate member and having a plurality of legs, wherein an end of a leg is configured to be selectively disconnectable from a portion of the retrieval assembly. The method further includes advancing the medical device to a desired body portion, extending the elongate member and retrieval assembly distally relative to the sheath to deploy the retrieval assembly, and entrapping the object within the retrieval assembly.

Various embodiments of the invention may include one or more of the following aspects: the method may further comprise the step of removing the medical device and entrapped object from the body; the step of extending the elongate member and retrieval assembly may include expanding the retrieval assembly; the step of deploying the retrieval assembly may include moving the sheath proximally relative to the elongate member; the elongate member may be connected to a proximal end of the retrieval assembly; the elongate member may move within the lumen of the sheath; the method may further comprise the step of disconnecting the end of the leg configured to be selectively disconnectable from the retrieval assembly; an end of each of two or more legs may be configured to be selectively disconnectable from the retrieval assembly; the elongate member and the retrieval assembly may comprise a one-piece construction; the device may further comprise a means for selectively disconnecting the end of the leg from the retrieval assembly; the selectively disconnecting means may include a portion of the leg configured to be received in an aperture in the portion of the retrieval assembly; the portion of the leg may be confined within the aperture by the sheath while the end of the leg is selectively connected to the portion of the retrieval assembly; the portion of the leg may be released from the aperture in response to movement of the elongate member relative the sheath; the step of disconnecting the end of the leg may include releasing a portion of the leg from an aperture located in the retrieval assembly; the step of disconnecting the end of the leg may include moving the elongate member relative to the sheath; moving the elongate member relative to the sheath may include retrieving the sheath proximally; moving the elongate member relative to the sheath may include extending the elongate member distally from the sheath; the end of the leg may be selectively connected to the portion of the retrieval assembly when the retrieval assembly is retracted within or extended from the lumen of the sheath; the end of the leg may be selectively connected to the portion of the retrieval assembly when the retrieval assembly is collapsed or expanded; the end of the leg selectively disconnectable from the portion of the retrieval assembly may be free from the portion of the retrieval assembly when disconnected.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description serve to explain the principles of the invention.

DESCRIPTION OF THE EMBODIMENTS

Figure 1:
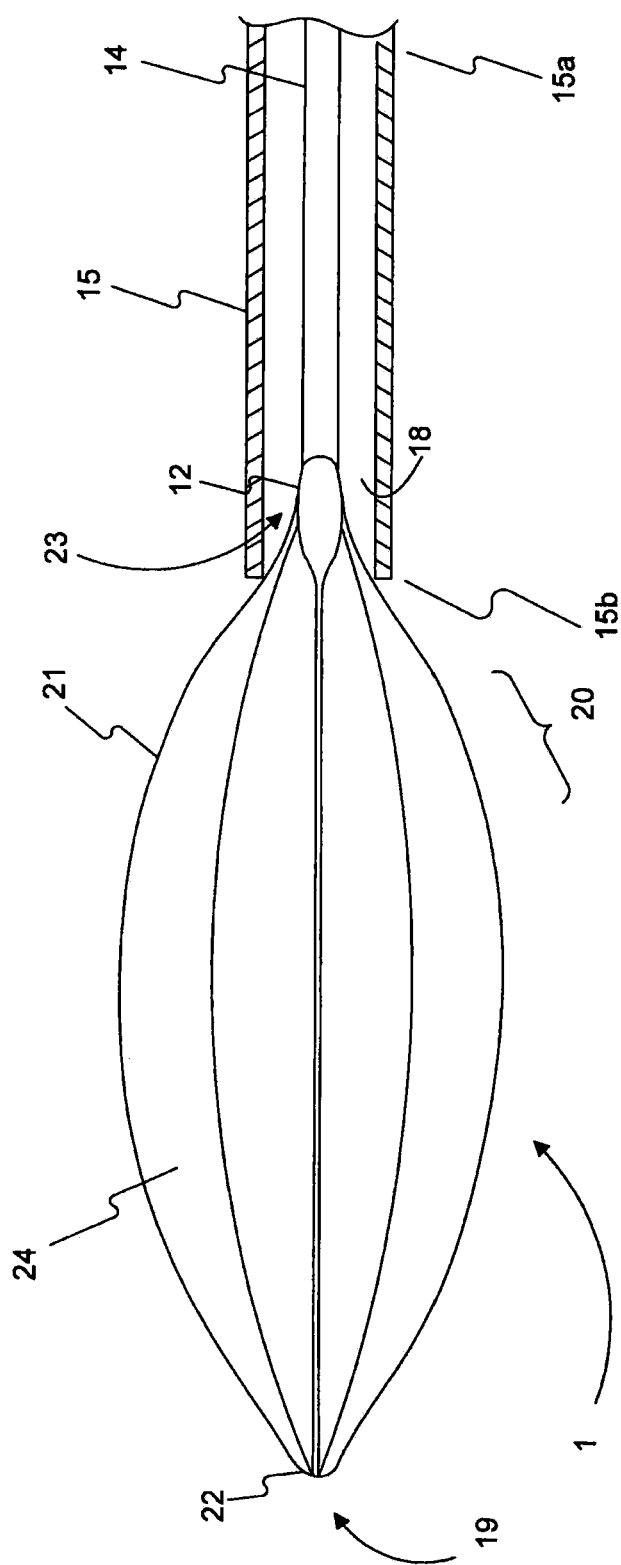
FIG. 1 is a schematic representation of a medical device in an expanded and extended position according to embodiments of the present invention.

Reference will now be made in detail to embodiments of the invention, an example of which is illustrated in the accompanying drawings. Wherever possible, the same reference numbers will be used throughout the drawings to refer to the same or like parts.

FIGS. 1-5 depict certain configurations of an exemplary embodiment of a medical device 1. The medical device 1 includes a sheath 15, an elongate member 14, and a retrieval assembly 20. As used in this disclosure, "distal" refers to a position or direction furthest from a user of the device and "proximal" refers to a position or direction opposite "distal" and closest to the user.

Sheath 15 includes a proximal end 15a and a distal end 15b, and may be any suitable sheath or catheter known in the art. Sheath 15 may be fabricated by any known process such as, for example, extrusion. In addition, sheath 15 may be made from any suitable material that provides sufficient strength and flexibility for adequate operation, but which is soft enough to avoid trauma or irritation to a body lumen in which sheath 15 may be deployed. Such materials may include, but are not limited to, polyurethane and/or silicone. Sheath 15 may have any desired cross-sectional shape and/or configuration. For example, sheath 15 may have a substantially circular cross-section. Sheath 15 may also have one or more cross-sectional shapes and/or configurations along its length, and may be any desired dimension suitable for deployment within a desired body lumen. For example, sheath 15 may have dimensions adapted for placement in a biliary duct having a particular size. For instance, sheath 15 may have an outer periphery that is substantially the same size as, or a size less than, the inner periphery of a biliary duct. The overall length and diameter of sheath 15 may vary depending on the application. For example, a relatively long sheath 15 may be advantageous for retrieving stones or other concretions deep within the body of a patient. Furthermore, sheath 15 may also be flexible along at least a portion of its length so that it may bend as it is advanced through tortuous body lumens.

Sheath 15 may further include at least one lumen 18 extending therethrough. In some embodiments, lumen 18 may be defined as an internal passageway with an entrance and an exit, and may be formed by any suitable process such as, for example, extrusion. Alternatively, sheath 15 may include a plurality of lumens (not shown) that may or may not differ in size. In such embodiments, the plurality of lumens may provide passageways useful in delivering, or removing, for example, medical devices, fluids, and/or other structures to or from a treatment site. Lumen 18 provided within sheath 15 may have any cross-sectional shape, dimension, and/or configuration. For example, in some embodiments, lumen 18 may have a substantially circular cross-section.

Elongate member 14 is longitudinally disposed and slideably moveable in lumen 18 of sheath 15. Elongate member 14 may be formed from, for example, a rod, tube, cannula, wire, stent, or other like structure. Alternatively, the elongate member 14 may also be formed from a portion of a cylindrical piece of material, or from a flat sheet of material. If formed from a flat sheet, elongate member 14 may be formed into a cylindrical shape to facilitate the fabrication of retrieval assembly 20.

Elongate member 14 may be formed from any biocompatible material known in the art. Such materials may include, but are not limited to, stainless steel, cobalt chromium, nickel, titanium, nitinol, thermoforming plastics, polytetrafluoroethylene (PTFE), and expanded polytetrafluoroethylene (EPTFE). In addition, elongate member 14 may also be a metal with one or more coatings such as, for example, a polymer.

Elongate member 14 may have any desired cross-sectional shape and/or configuration. For example, elongate member 14 may have a substantially circular cross-section. In addition, elongate member 14 may have one or more cross-sectional shapes and/or configurations along its length, and may have any desired dimension suitable for deployment in a desired body lumen, and retraction into sheath 15. For example, elongate member 14 may have an outer periphery that facilitates insertion into sheath 15, and permits longitudinal movement of elongate member 14 relative to sheath 15. The overall length and diameter of elongate member 14 may vary depending on the application. For example, a relatively long elongate member 14 may be advantageous for retrieving stones or other unwanted objects deep within the body of a patient. In addition, elongate member 14, having a relatively small diameter, may be advantageous for retrieving stones from restricted passageways within the human urinary tract.

Elongate member 14 may include a number of any desired flexibility features (not shown) to increase maneuverability of the device 1 while the device 1 is within the body of a patient. The flexibility features, for example, may be cut into a distal portion of elongate member 14. However, flexibility features may be positioned anywhere along the length of the elongate member 14, and may be created by any suitable process known in the art.

In some embodiments, elongate member 14 may further include one or more internal lumens (not shown) extending therethrough. In such embodiments, the lumens may provide passageways useful in delivering, or removing, for example, medical devices such as laser fibers, fluids, and/or other structures to or from a treatment site.

Retrieval assembly 20 extends distally from a distal end of elongate member 14, and may be, for example, a basket having a distal portion 19, a proximal portion 23, and any desired number of legs 21. In addition, retrieval assembly 20 may be retractable within and extendable from lumen 18 of sheath 15. The retrieval assembly 20 may be manufactured from any suitable biocompatible material, for example, one or more metals and/or composites, such as, but not limited to, 400 series stainless steel, Ti-Beta-3 titanium alloys, cobalt chromium alloys, and nitinol. Retrieval assembly 20 may have any desired cross-sectional shape and/or configuration. For example, retrieval assembly 20 may have a substantially circular cross-section. Retrieval assembly 20 may also have one or more cross-sectional shapes and/or configurations along its length, and any desired dimensions suitable for deployment in a desired body lumen. For example, retrieval assembly 20 may have dimensions adapted for placement in a biliary duct having a particular size. For instance, retrieval assembly 20, in an expanded state, may have an outer periphery that is substantially the same size as, or less than, the inner periphery of a biliary duct. In addition, retrieval assembly 20 may have configurations, dimensions, and/or material properties that permit longitudinal movement of retrieval assembly 20 relative to sheath 15 and extension and retraction into and out of sheath 15. The overall length and diameter of retrieval assembly 20 may vary depending on the application. For example, a relatively small diameter may be advantageous for retrieving stones or other unwanted objects from restricted passageways within the human urinary tract. Retrieval assembly 20 may also be collapsible so that it may be more easily advanced through body lumens in its collapsed state, and when desired, expandable for deployment. For example, retrieval assembly 20 may be made from certain materials and according to certain methods so that retrieval assembly 20 may self-expand when extended from lumen 18 of sheath 15, as is known in the art. Alternatively, retrieval assembly 20 may be expanded in any other suitable manner known in the art.

Retrieval assembly 20 may be made out of the same piece of material as elongate member 14. Alternatively, retrieval assembly 20 may be fabricated independently by any known means, and may then be made integral with elongate member 14 through connection of proximal end 23 of retrieval assembly 20 to a region of elongate member 14, such as a distal end of elongate member 14. Connection of proximal end 23 to elongate member 14 may be accomplished through any suitable means of fixedly connecting retrieval assembly 20 to elongate member 14. For example, possible connections may include, but are not limited to, welding, soldering, and/or crimping.

Legs 21 of retrieval assembly 20 may be formed by, for example, laser cutting, chemical etching, die cutting, or mechanically slicing a single piece of material. As a result, the width of the cuts may define the width and mechanical behavior of each of the legs 21, and the desired width of the cuts may vary depending on the particular application. For example, it may be advantageous to have relatively narrow basket legs 21 when retrieving a relatively large stone from within the body. In certain instances, legs 21 may be formed by, for example, welding, soldering, tying, or otherwise connecting separate pieces of wire or other material together. In such instances, legs 21 may or may not be made with the same materials.

Although FIG. 1 shows that retrieval assembly 20 comprises 6 legs, retrieval assembly 20 may include any number of legs to facilitate retrieval of unwanted objects from within a patient's body. Legs 21 may have any desired pattern, configuration, and characteristic suitable for entrapping objects within an anatomical lumen. For example, legs 21 may be cylindrical, flat, square, semi-circular, rectangular, or any other shape suitable to entrapping objects from within a patient's body. In addition, legs 21 may be any cross-sectional shape known in the art including, but not limited to, circular, flat, square, or ovular. Additionally, legs 21 may be made of a material exhibiting shape memory, as is known in the art.

In some embodiments, at least a portion of at least one of the legs 21 may include an inward facing surface textured to improve the stone retrieval capabilities of device 1. For example, possible structures that may be used as texture may include, but are not limited to, indentations, teeth, spikes, treads, and serrations. The texture of the inward facing surface may provide multi-point contact with objects targeted for entrapment and may be pointed away from the sensitive tissue within the body structure so as not to cause trauma thereto. Furthermore, at least a portion of at least one of the legs 21 may be coated with, for example, a layer of PTFE, EPTFE, polyvinylethylene, or any other material suitable for protecting legs 21 during processes such as, for example, laser lithotripsy.

Retrieval assembly 20 may include a plurality of cells or spaces 24 between legs 21. Spaces 24 may be of any suitable shape, size, and/or configuration, and may be configured to accommodate and allow objects to pass into the interior of the retrieval assembly 20 for entrapment and, if desired, subsequent removal from the body. Furthermore, the sizes of spaces 24 between legs 21 may vary or be consistent.

The distal end of each of legs 21 may connect to tip 22. Tip 22 may further be sized and shaped to assist in the capture and retrieval of stones within a patient's body. For example, tip 22 may be blunt, rounded, flat, smooth, knotted, or any other atraumatic shape known in the art, and may or may not be composed of the same material as legs 21. Tip 22 may be as small as possible so as not to interfere with the capture and retrieval of the targeted stone. Furthermore, tip 22 may be formed by soldering, welding, cementing, tying, or otherwise connecting the distal ends of legs 21 together, and may or may not contain fillers such as, for example, epoxy.

Figure 4:
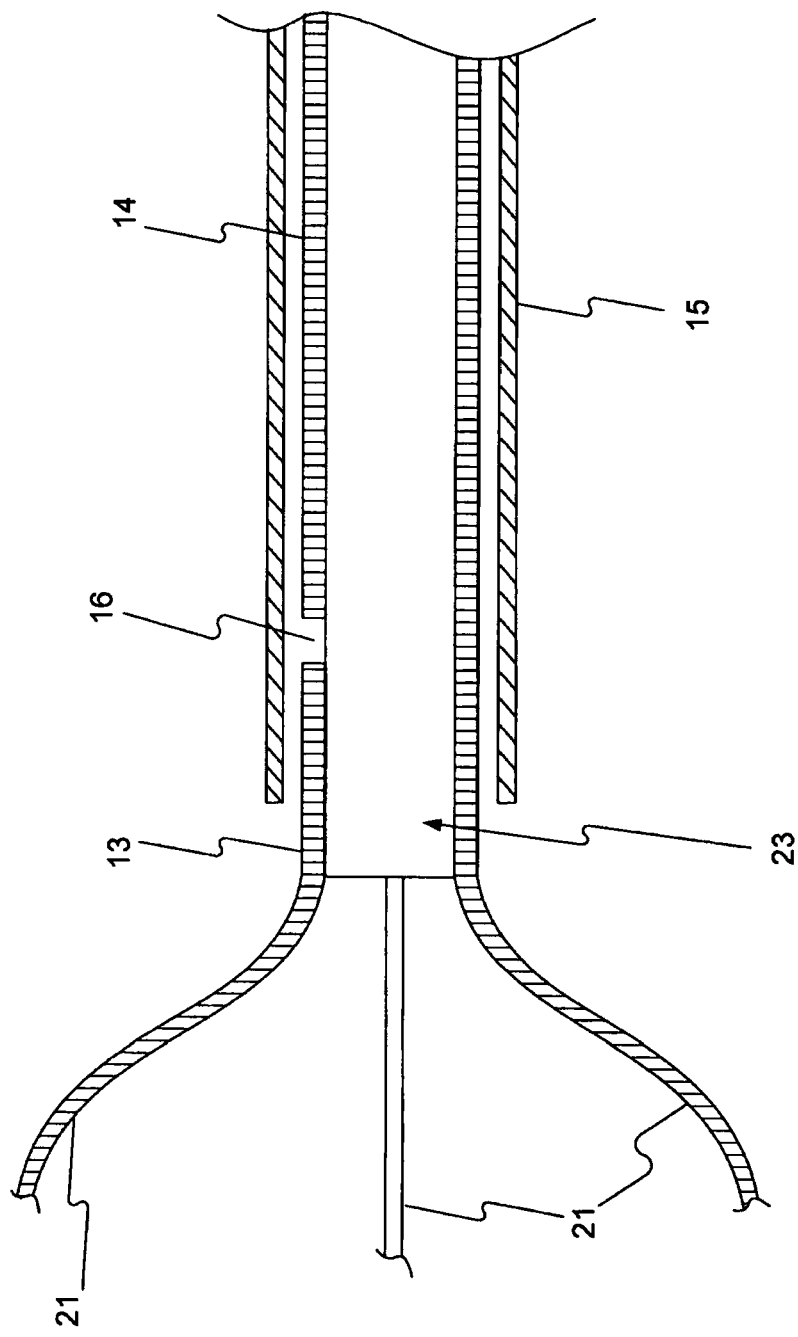
FIG. 4 is a cross-sectional view along line A-A of a portion of the device in FIG. 1 with a leg releasably connected to the device.

In accordance with embodiments of the present invention, at least one of the legs 21 may have a first state in which a proximal end of the leg 21 is releasably connected to a portion of the retrieval assembly 20 and/or elongate member 14, and a second state in which the proximal end of the leg 21 is disconnected from the portion of the retrieval assembly 20 and/or elongate member 14. For example, the proximal end of at least one of legs 21 may be releasably connected to proximal end 23 of the retrieval assembly 20 and/or a distal end of elongate member 14. The proximal end of a leg 21 may be releasably connected to proximal end 23 by means of connection 12 or through any other suitable means known in the art. As shown in FIG. 4, the exemplary connection 12 comprises a key 13 (such as an extension or protrusion) located at the proximal end of a leg 21 and a key way 16 (such as a space or aperture) located in proximal end 23. The key way 16 may correspond to the shape and size of the key 13 such that the key way 16 is configured to receive the key 13. In addition, the key 13 may be releasably maintained within key way 16 by sheath 15 when leg 21 is releasably connected to proximal end 23.

Figure 5:
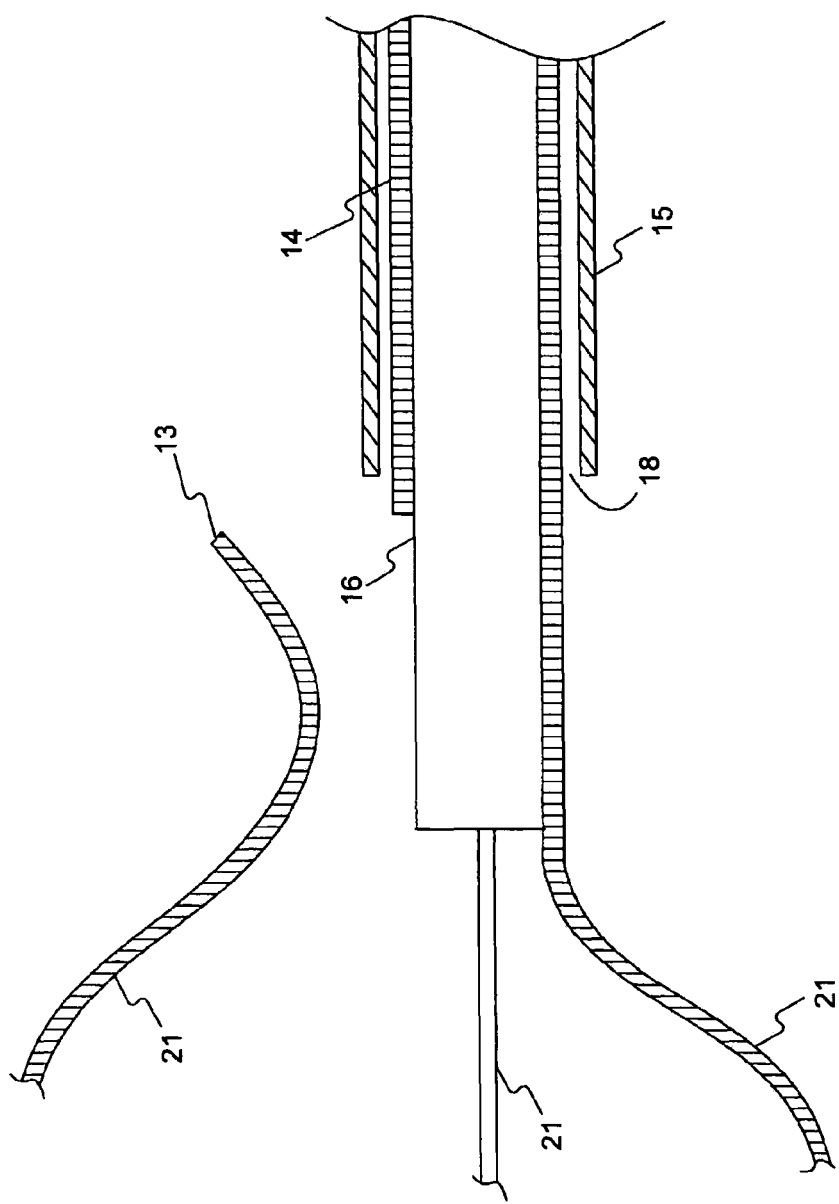
FIG. 5 is a cross-sectional view along line A-A of a portion of the device in FIG. 1 with a leg selectively disconnected from the device.

Key 13 and key way 16 may be created by any suitable means known in the art. For example, possible means may include, but are not limited to, stamping, welding, laser cutting, chemical etching, and die cutting. In addition, key 13 and key way 16 may be of any suitable size and/or shape. Although FIGS. 4 and 5 show the connection 12 provided on only one of legs 21, the number of legs releasably connected to proximal end 23 by means of a connection 12, or any other means of releasably connecting the legs 21 to the proximal end 23, may vary depending on the application.

As will be discussed in greater detail below, in certain circumstances it may be desirable to release one or more of legs 21 of retrieval assembly 20. In such circumstances, legs 21 may be made from any suitable material that facilitates the release of legs 21, for example, by providing elasticity, shape memory characteristics, or a spring-like nature to legs 21 and/or placing legs 21 under continuous tensile stress. For example, legs 21 may be made from a material that possesses shape memory characteristics such as, for example, Nitinol. The proximal end of a leg 21 may be disengaged from the proximal end 23 by distally advancing elongate member 14 relative to sheath 15 such that sheath 15 no longer covers key 13, and key 13 is allowed to escape the confines of key way 16.

Alternatively, the connection 12 of a leg 21 to proximal end 23 may be configured in a manner that allows a suitable actuator at the proximal user end of sheath 15 to disengage a leg 21 from proximal end 23 of retrieval assembly 20.

Embodiments of the present invention may also be configured to allow a user to view the distal region of elongate member 14 and/or sheath 15. For example, sheath 15 may be fabricated from a translucent material so that a user may view the position of the connection 12 through sheath 15 and relative to sheath 15. As another example, the distal region may include markers, such as radiopaque markers, at appropriate positions to indicate the relative positions of elongate member 14 and sheath 15. The user may utilize any suitable viewing means known in the art such as, for example, an endoscope. In such configurations, the user may monitor the position of the connection 12 relative to the distal edge of sheath 15, and is therefore able to prevent accidental overextension of elongate member 14 and the accidental disconnection of any of legs 21.

The connection 12 for releasably connecting a leg 21 to the proximal end 23, shown and described in FIGS. 1-5, may be used with suitable medical or non-medical devices capable of entrapping, releasing, and/or removing objects from any location in which a passageway or orifice includes unwanted material to be removed and/or is being partially blocked, including devices used in urologic, endoscopic, or other like procedures. For example, such devices include, but are not limited to, stents, snares, baskets, and embolic protection devices.

Retrieval assembly 20, shown and described in FIGS. 1-5, is an exemplary retrieval assembly that may be used in the method and device of the present invention. Any other suitable retrieval assembly capable of entrapping, releasing, and/or removing objects from within a body lumen may be used.

Figure 2:
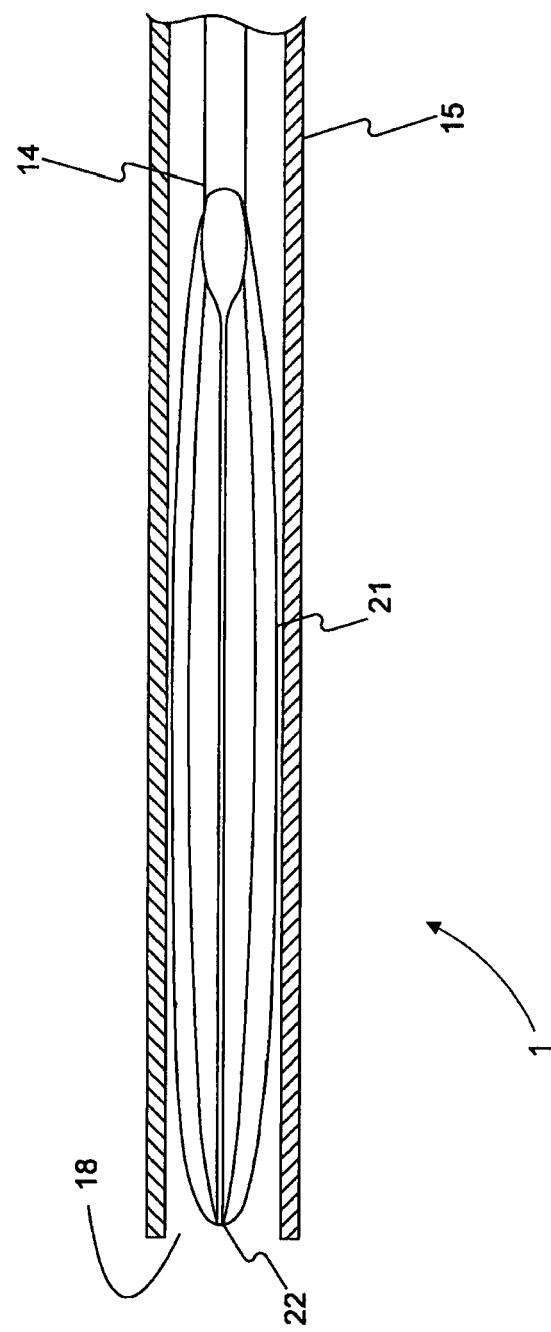
FIG. 2 is a schematic representation of the device in FIG. 1 in a retracted and collapsed position.
Figure 3:
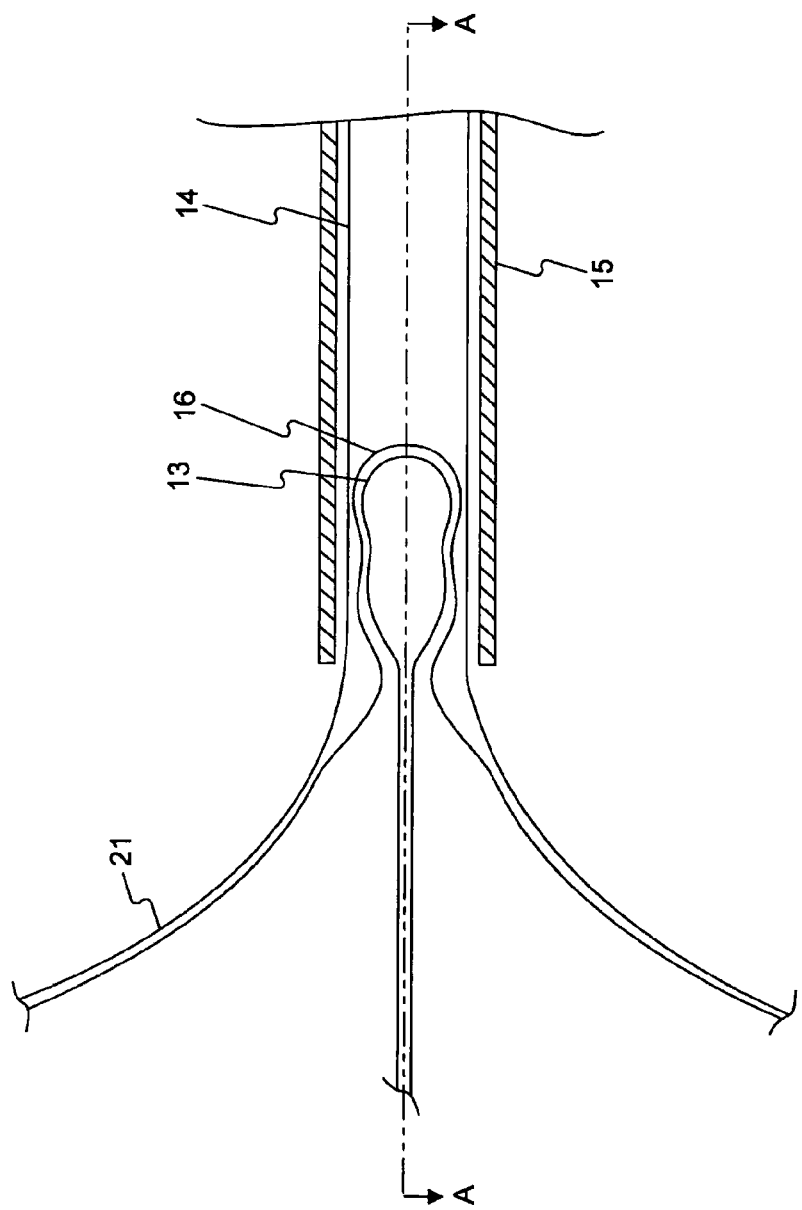
FIG. 3 is a top view of a portion of the device in FIG. 1 with a leg releasably connected to the device.

As shown in FIGS. 1-2, retrieval assembly 20 may be configured to collapse and expand as desired. For example, retrieval assembly 20 may be configured to be collapsible such that it facilitates retraction into lumen 18 of sheath 15 as shown in FIG. 2, and/or advanced out of sheath 15, such that retrieval assembly 20 at least partially expands and/or fully expands as shown in FIG. 1. In such an example, retrieval assembly 20 may be collapsed and retracted into lumen 18 of sheath 15, while sheath 15 is being advanced through a body lumen to a desired body location. Once sheath 15 is positioned at the desired body location, retrieval assembly 20 may be advanced out of sheath 15 for expansion.

Retrieval assembly 20 may be retracted into and/or advanced out of lumen 18 of sheath 15 using any method known in the art. For example, by means of the connection between proximal end 23 and elongate member 14, movement of elongate member 14 relative to sheath 15 causes retrieval assembly 20 to also move relative to sheath 15 allowing retrieval assembly 20 to be retracted into and/or advanced out of sheath 15. Any suitable known handle assemblies may be used at the proximal user end of sheath 15 and/or elongate member 14 for actuation.

In reference to FIGS. 1-5, embodiments of the invention may include methods of using the medical device 1 of the present disclosure to retrieve stones and other unwanted materials located in the bladder, ureter, kidney, or other body structures. Medical device 1 may be used in an environment that is relatively fluid filled or that is relatively dry. The medical device 1 may be inserted through the urethra of a patient or, alternatively, the medical device 1 may be inserted percutaneously. The medical device 1 may be used in any location of the body in which a passageway or orifice includes unwanted material to be removed and/or is being at least partially blocked.

The medical device 1 may be advanced to a treatment site in a number of different ways. For example, the device 1 may be advanced to a desired body location over a guide wire (not shown), wherein the desired body location may correspond to the vicinity of a stone or another object targeted for removal. The medical device 1 may also be advanced to the treatment sire through an access sheath or any other access device known in the art.

Alternatively, the medical device 1 may be fed to the desired body location by means of an imaging device, and may travel through the body without the use of a guide wire or access sheath. To facilitate such feeding, sheath 15 may include radiopaque marker bands (not shown) detectable by x-ray or other imaging means. Thus, the user may monitor the position of the device 1 and movement thereof through the use of an imaging device.

As yet another alternative, the device 1 may be used in conjunction with an endoscope (not shown) or any other type of intracorporeal scope known in the art. The endoscope may travel through the body to the treatment site in any conventional manner. Once the endoscope is positioned adjacent to the treatment site, the medical device 1 may be fed through an access port of the endoscopic sheath to gain access to the object targeted for retrieval, such as a stone.

Although not shown, the object targeted for retrieval may be a bodily concretion such as, for example, a stone. The object targeted for retrieval may include, but is not limited to, kidney stones, gallbladder stones, uric acid stones, or other solids commonly removed from a body structure or passageway. The objects may be of any size and/or shape. Furthermore, the medical device 1 may be used to retrieve objects that are both impacted and free floating.

In clinical applications where an endoscope (not shown) or other similar access device is used for access, the endoscope may be advanced through a tortuous body lumen and past a desired body location. With retrieval assembly 20 disposed inside of sheath 15 and in a collapsed and retracted state, the medical device 1 may then be inserted into the body lumen by feeding the medical device 1 through an access port in the endoscopic sheath to the desired body location. For example, the medical device 1 may be advanced until the distal end of sheath 15 has reached a desired location, such as, a short distance past an object targeted for entrapment and/or removal. The method is not limited to the use with any particular object, and may also be used with one or more intracorporeal and/or extracorporeal objects at various locations and of various geometries and compositions.

Once the distal end of sheath 15 is advanced past a targeted object, the elongate member 14 may then be advanced distally out of sheath 15, so that retrieval assembly 20 may deploy and self-expand. For example, this may be achieved by pulling sheath 15 proximally relative to elongate member 14. Any suitable known handle assemblies may be used to effect deployment and expansion of retrieval assembly 20. When fully deployed, retrieval assembly 20 may be substantially cylindrically shaped or have any other configuration suitable to the particular size and shape of both the targeted object and/or the environment it is located in. The proximal end 23 of retrieval assembly may remain in a collapsed state and/or disposed within sheath 15, and may be the narrowest portion of retrieval assembly 20.

Once elongate member 14 has been sufficiently advanced out of sheath 15 to allow at least partial deployment and/or expansion of retrieval assembly 20, the medical device may be moved proximally, and sometimes repeatedly, such that the object targeted for entrapment passes through spaces 24 and becomes entrapped within retrieval assembly 20.

The medical device, along with the entrapped object, may then be moved to any desired location, or may be allowed to remain stationary. For example, the medical device 1 may be used as an extraction device and removed from the body, assist in immobilizing objects and used as a backstop, or moved to a location more conducive to any additional procedures, such as lithotripsy, surgery, or any other process known in the art.

In certain circumstances, it may be desired to release the entrapped object after it has been captured in retrieval assembly 20. To do so, elongate member 14 may be further advanced distally out of sheath 15 to disengage one or more of legs 21. For example, this may be accomplished by pulling sheath 15 proximally relative to elongate member 14 and connection 12 so that sheath 15 no longer prevents the disengagement of key 13 from key way 16, and, consequently, the disconnection of a leg 21 from the proximal end 23. Subsequently, the medical device may then be gently agitated or otherwise maneuvered to allow the entrapped object to exit retrieval assembly 20.

If desired, any disconnected legs 21 may again be connected to proximal end 23 of retrieval assembly 20 so that another targeted object may become entrapped within retrieval assembly 20. Legs 21 may be reconnected to the proximal end 23 by any suitable structure and through any suitable method. Furthermore, the medical device 1 may also be re-used with the same patient, for example, by retracting elongate member 14 and recollapsing retrieval assembly 20 within sheath 15 and repositioning or reinserting the medical device 1 in the body.

By way of example, one advantage of using retrieval assembly 20 with a selectively disconnectable leg 21 is that in cases where the entrapped object may be too large for successful removal from the body, the object may be released and the medical device 1 may be safely removed from the body.

Embodiments of the invention may be used in any medical or non-medical procedure, including any medical procedure wherein removal of an object from within a body lumen is desired. In addition, at least certain aspects of the aforementioned embodiments may be combined with other aspects of the embodiments, or removed, without departing from the scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
a sheath having a proximal end, a distal end, and a lumen extending longitudinally between the proximal and distal ends;
an elongate member extending within the lumen of the sheath and moveable relative to the sheath; and
a retrieval assembly, a proximal end of the retrieval assembly connected to a distal region of the elongate member, retractable within and extendable from the lumen of the sheath, and having a plurality of legs comprising at least a first leg, a second leg, and a third leg, wherein a proximal end of the first leg is selectively disconnectable from a portion of the retrieval assembly in direct response to movement of the elongate member relative to the sheath,
wherein at least the second and third leg does not disconnect from the portion of the retrieval assembly in direct response to movement of the elongate member relative to the sheath; and
wherein a distal end of each of the plurality of legs is connected to each other at a tip.

2. The device of claim 1, wherein the elongate member and the retrieval assembly are formed of a single member.

3. The device of claim 1, wherein a portion of the first leg is configured to be received in an aperture in the portion of the retrieval assembly.

4. The device of claim 3, wherein the portion of the first leg is released from the aperture in direct response to movement of the elongate member relative to the sheath.

5. The device of claim 4, wherein the sheath is moved proximally relative to the elongate member to release the portion of the first leg from the aperture.

6. The device of claim 1, wherein the proximal end of the first leg is configured to be selectively connected to the portion of the retrieval assembly when the retrieval assembly is retracted within the lumen of the sheath.

7. The device of claim 1, wherein the portion of the retrieval assembly does not disconnect from the elongate member when the first leg is disconnected from the portion of the retrieval assembly.

8. The device of claim 1, wherein the second leg is configured to remain fixed to the portion of the retrieval assembly when the portion of the retrieval assembly extends out of the lumen of the sheath.

9. A medical device comprising:
a sheath having a proximal end, a distal end, and a lumen extending longitudinally between the proximal and distal ends;
an elongate member extending within the lumen of the sheath and moveable relative to the sheath; and
a retrieval assembly having a proximal end, a distal end, and a plurality of legs including at least a first leg, a second leg, and a third leg, each leg having connections at the proximal and distal ends of the retrieval assembly, the proximal end of the retrieval assembly being connected to a distal region of the elongate member and retractable within and extendable from the lumen of the sheath, wherein a proximal end of the first leg is configured to be selectively disconnected from a portion of the retrieval assembly;
wherein a distal end of each of the plurality of legs is connected to each other at a tip;
wherein the sheath and elongate member are flexible so as to traverse tortuous anatomy of a patient; and
wherein at least the second leg does not disconnect from the portion of the retrieval assembly in direct response to movement of the elongate member relative to the sheath.

10. The device of claim 9, wherein the retrieval assembly is configured to be substantially collapsed when retracted into the sheath and expanded when extended from the sheath.

11. The device of claim 9, wherein the third leg is configured to be selectively disconnected from the portion of the retrieval assembly.

12. The device of claim 9, wherein the first leg is configured to be disconnected in response to movement of the elongate member relative to the sheath.

13. The device of claim 9, wherein the sheath is moved proximally relative to the elongate member to disconnect the portion of the first leg from the portion of the retrieval assembly.

14. The device of claim 9, wherein the proximal end of the first leg configured to be selectively disconnected is free from the portion of the retrieval assembly when in a disconnected state.

15. A medical device comprising:
a sheath having a proximal end, a distal end, and a lumen extending longitudinally between the proximal and distal ends;
an elongate member extending within the lumen of the sheath and moveable relative to the sheath; and
a retrieval assembly, a proximal end of the retrieval assembly connected to a distal region of the elongate member, retractable within and extendable from the lumen of the sheath, and including a plurality of legs, wherein a first leg of the plurality of legs has a first state in which a proximal end of the first leg is connected to a portion of the retrieval assembly and second state in which the proximal end of the first leg is disconnected from the portion of the retrieval assembly;
wherein the plurality of legs further comprises at least a second leg and a third leg;
wherein a distal end of each of the plurality of legs is connected to each other at a tip; and
wherein the second leg does not disconnect from the portion of the retrieval assembly in direct response to movement of the elongate member relative to the sheath.

16. The device of claim 15, wherein a portion of the first leg releasably connected to the portion of the retrieval assembly is configured to be received in or released from an aperture in the portion of the retrieval assembly.

17. The device of claim 15, wherein the retrieval assembly is configured to be substantially collapsed when retracted into the sheath and expanded when extended from the sheath.

18. The device of claim 15, wherein the third leg has a first state in which a proximal end of the third leg is releasably connected to the portion of the retrieval assembly and a second state in which the proximal end of the third leg is disconnected from the portion of the retrieval assembly.

19. The device of claim 15, wherein the portion of the retrieval assembly is not configured to detach from the elongate member when the retrieval assembly is in a body.

* * * * *